United States Patent
Durfee

(10) Patent No.: US 10,449,113 B2
(45) Date of Patent: Oct. 22, 2019

(54) SYSTEM FOR TRANSPORTING A SAUNA DEVICE

(71) Applicant: Eileen Durfee, Kennewick, WA (US)

(72) Inventor: Eileen Durfee, Kennewick, WA (US)

(73) Assignee: Creatrix Solutions LLC, Kennewick, WA (US)

( * ) Notice: Subject to any disclaimer, the term of this patent is extended or adjusted under 35 U.S.C. 154(b) by 54 days.

(21) Appl. No.: 15/791,141

(22) PCT Filed: Jun. 28, 2016

(86) PCT No.: PCT/IB2016/053856
§ 371 (c)(1),
(2) Date: Oct. 23, 2017

(87) PCT Pub. No.: WO2017/002015
PCT Pub. Date: Jan. 5, 2017

(65) Prior Publication Data
US 2018/0168926 A1    Jun. 21, 2018

Related U.S. Application Data

(60) Provisional application No. 62/186,650, filed on Jun. 30, 2015.

(51) Int. Cl.
*B65D 85/42* (2006.01)
*A61H 33/06* (2006.01)
(Continued)

(52) U.S. Cl.
CPC .......... *A61H 33/063* (2013.01); *A45C 11/00* (2013.01); *A45C 11/24* (2013.01); *A45C 13/02* (2013.01);
(Continued)

(58) Field of Classification Search
CPC ...... A61H 33/06; A61H 33/063; A61H 37/00; A61H 2201/0153; A61H 2201/0157;
(Continued)

(56) References Cited

U.S. PATENT DOCUMENTS 5,950,254 A * 9/1999 Yasue ............... A61H 33/063
                                                      4/524
6,031,321 A * 2/2000 Park ....................... H01K 1/18
                                                      313/238
(Continued)

*Primary Examiner* — Luan K Bui

(57) ABSTRACT

A system for transporting a sauna device is used for storing and transporting an infrared sauna lamp. The system includes an infrared sauna lamp and a sealable carrying bag. The infrared sauna lamp emits heat and light used for therapeutic healing. The sealable carrying bag is used to store, protect, and transport the infrared sauna lamp. The sealable carrying bag includes a flexible receptacle, a lid, a first handle and a second handle. The infrared sauna lamp is placed within the flexible receptacle during transport. The lid is connected to the flexible receptacle and is used to close the sealable carrying bag. The first handle and the second handle connect to the flexible receptacle and are used to carry the sealable carrying bag. A first pouch, a second pouch, and a third pouch are placed within the flexible receptacle to carry various items associated with the infrared sauna lamp.

9 Claims, 10 Drawing Sheets

(51) Int. Cl.
*A45C 11/00* (2006.01)
*A45C 11/24* (2006.01)
*A45C 13/02* (2006.01)
*B32B 1/00* (2006.01)
*B32B 1/02* (2006.01)
*A61H 37/00* (2006.01)
*A61N 5/06* (2006.01)

(52) U.S. Cl.
CPC ................ *B32B 1/00* (2013.01); *B32B 1/02* (2013.01); *A61H 33/06* (2013.01); *A61H 37/00* (2013.01); *A61H 2201/0153* (2013.01); *A61H 2201/0157* (2013.01); *A61H 2201/10* (2013.01); *A61N 2005/0659* (2013.01); *A61N 2005/0668* (2013.01); *B32B 2439/46* (2013.01)

(58) Field of Classification Search
CPC ......... A45C 11/00; A45C 11/24; A45C 13/02; A61N 2005/0659; A61N 2005/0668
USPC ......... 206/234, 442, 419; 4/524, 527; 383/6, 383/61.1, 61.3, 104
See application file for complete search history.

(56) References Cited

U.S. PATENT DOCUMENTS

| | | | |
|---|---|---|---|
| 6,170,097 B1* | 1/2001 | Lin | A61H 33/06 4/524 |
| 7,815,024 B1* | 10/2010 | Quimpo | A45C 7/0036 190/107 |
| 2002/0181806 A1* | 12/2002 | Godshaw | A01K 97/06 383/6 |
| 2008/0196152 A1* | 8/2008 | Lozano | A61H 33/06 4/527 |
| 2012/0294550 A1* | 11/2012 | Hassman | A45C 3/001 383/6 |
| 2014/0177980 A1* | 6/2014 | Diao | B65D 88/1612 383/6 |
| 2015/0147006 A1* | 5/2015 | Beatty | A45C 7/0063 383/6 |

* cited by examiner

US 10,449,113 B2

SYSTEM FOR TRANSPORTING A SAUNA DEVICE

The current application is a 371 of international Patent Cooperation Treaty (PCT) application PCT/IB2016/053856 filed on Jun. 28, 2016. The PCT application PCT/IB2016/053856 claims benefit of a U.S. provisional patent application Ser. No. 62/186,650 filed on Jun. 30, 2015.

FIELD OF THE INVENTION

The present invention relates generally to bags and protective carrying cases thereof. In particular, the present invention is a sealable carrying bag generally used for the transportation and protection of a portable near infrared sauna light panel or array and other various equipment.

BACKGROUND OF THE INVENTION

Near infrared saunas are saunas powered by the "near" wavelengths of the infrared spectrum. These devices are generally used indoors with or in enclosures or tent like devices, used for therapeutic healing through heat application, as an alternative to steam and far infrared saunas. Near infrared saunas comprise light arrays, in the form of near infrared lamps or bulbs that screw into electrical socket housings that are attached to panels. Near infrared saunas are somewhat bulky in structure, as well as expensive and sometimes difficult to transport, as they often include chains or similar devices used to hang the sauna from ceilings, walls, and doors; or clamp to tent poles, or screw or fasten inside traditional saunas. As such, there exists a need for a carrying bag or case for near infrared saunas.

It is therefore an objective of the present invention to introduce a sealable carrying bag for near infrared saunas. The sealable carrying bag of the present invention is durable and protective and is dimensioned to house diamond and rectangular shaped near infrared saunas with three or four bulb configurations. The sealable carrying bag may be manufactured to fit other shapes, including but not being limited to that of a triangle, parallelogram, pentagon, and more, as well as additional bulbs. The present invention is generally used to house a near infrared sauna, without the need to remove the infrared bulbs. The bulbs are generally 250-watt heat lamp bulbs, however, this may vary. The present invention also includes the use of smaller removable pouches that fit inside the bag. Overall, the present invention provides a convenient way to store, protect, and transport a portable near infrared sauna.

DETAIL DESCRIPTIONS OF THE INVENTION

Figure 1:
FIG. 1 is top perspective view of the present invention with the lid closed.

With reference to FIGS. 1-6, the present invention is a system for transporting a sauna device. The present invention is used to safely store and transport an infrared sauna lamp 1. The present invention comprises an infrared sauna lamp 1 and a sealable carrying bag 2. The infrared sauna lamp 1 uses near infrared wavelengths of light to apply heat for therapeutic healing. The sealable carrying bag 2 helps to transport the infrared sauna lamp 1 and prevent the infrared sauna lamp 1 from being damaged. The sealable carrying bag 2 comprises a flexible receptacle 3, a lid 12, a first handle 13, and a second handle 14. The flexible receptacle 3 is used to surround the infrared sauna lamp 1 in order to prevent damage to the infrared sauna lamp 1. The flexible receptacle 3 comprises a lateral portion 4 and a base portion 8. The base portion 8 helps to reinforce and give structure to the flexible receptacle 3. The lateral portion 4 helps to secure the infrared sauna lamp 1 within the flexible receptacle 3. The lateral portion 4 is perimetrically connected to the base portion 8. A rim 5 of the lateral portion 4 is perimetrically positioned about the lateral portion 4, opposite to the base portion 8. The lid 12 is hingedly connected to the rim 5. The lid 12 is used to prevent the infrared sauna lamp 1 from shifting within the flexible receptacle 3 or falling out of the flexible receptacle 3. The first handle 13 is laterally connected to the lateral portion 4, in between the base portion 8 and the rim 5. The second handle 14 is laterally connected to the lateral portion 4, in between the base portion 8 and the rim 5. Together, the first handle 13 and the second handle 14 are used to carry the infrared sauna lamp 1 within the flexible receptacle 3. The first handle 13 and the second handle 14 are positioned opposite to each other about the lateral portion 4. This arrangement helps to equally distribute the weight of the infrared sauna lamp 1 when the infrared sauna lamp 1 is being carried. When storing or transporting the infrared sauna lamp 1, the infrared sauna lamp 1 is positioned within the sealable carrying bag 2. The lid 12 is secured to the flexible receptacle 3 for added protection.

Figure 3:
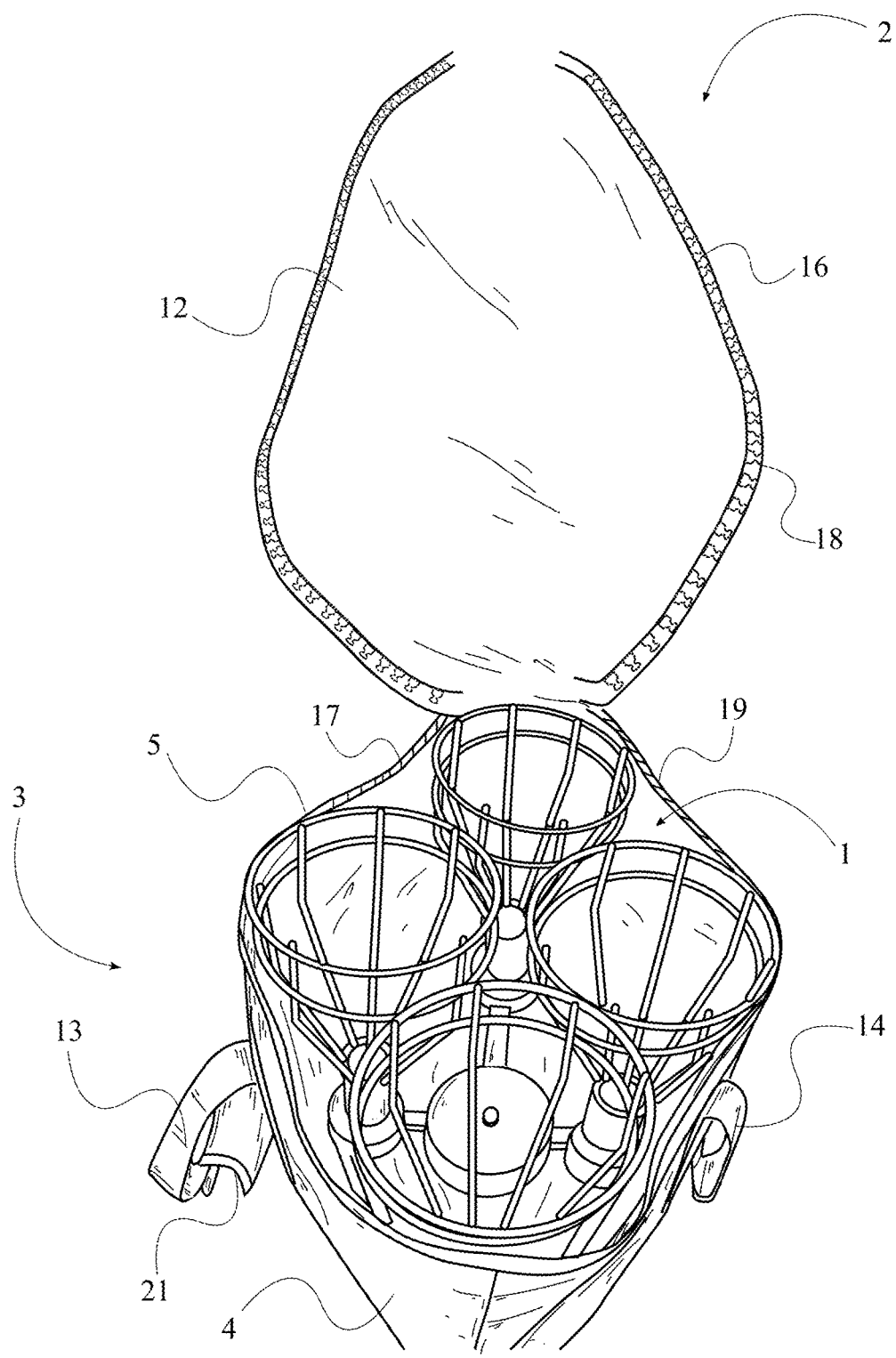
FIG. 3 is a top perspective view of the present invention with the lid open.
Figure 5:
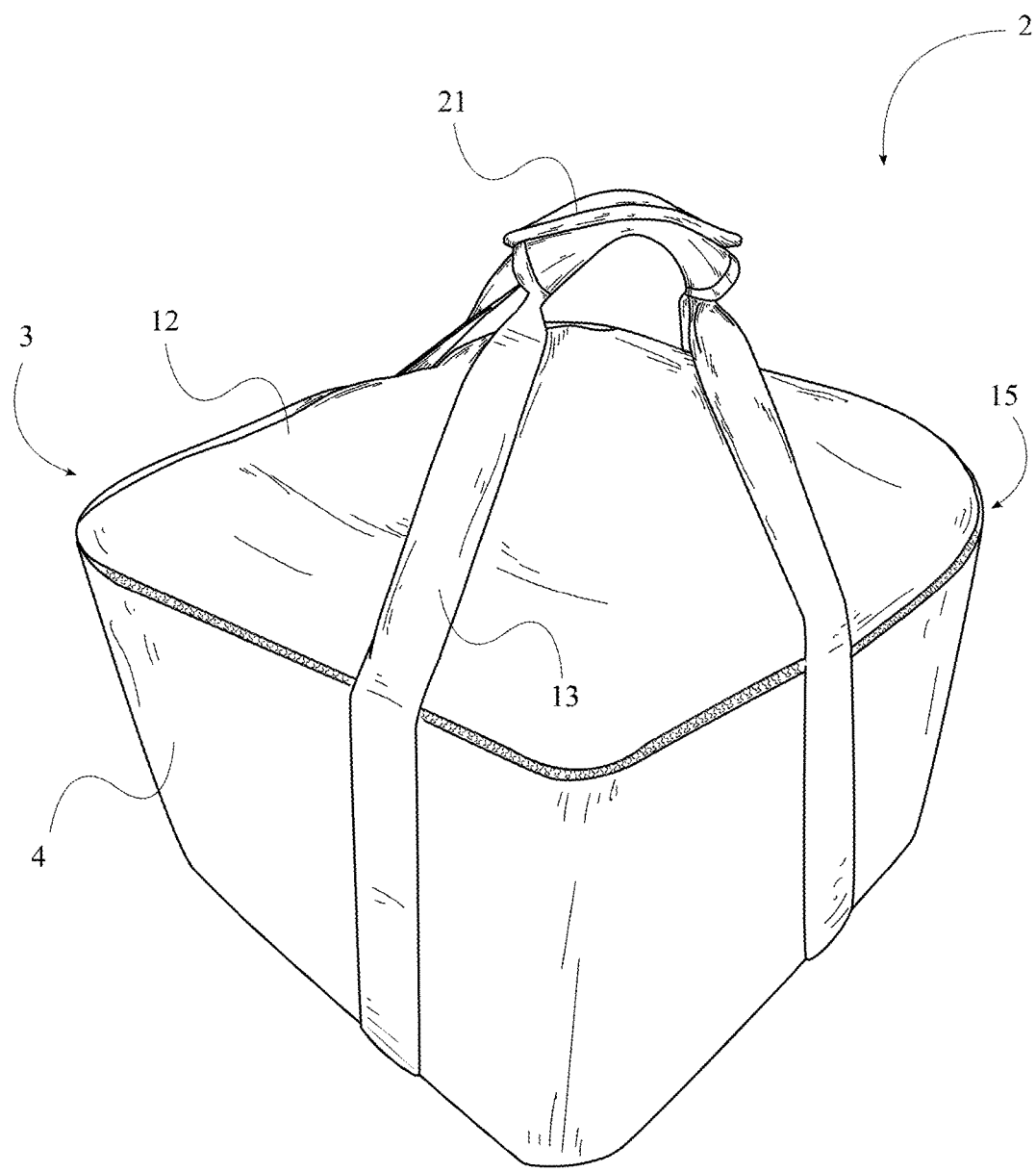
FIG. 5 is a side perspective view of the present invention with the first handle and the second handle attached to each other with the handle grip.

In reference to FIG. 3 and FIG. 5, the present invention further comprises a lid fastener 15. The lid fastener 15 is used to secure the lid 12 to the flexible receptacle 3 in order to close the sealable carrying bag 2. The lid fastener 15 comprises a first engaging portion 16 and a second engaging portion 17. The first engaging portion 16 is perimetrically connected to the lid 12 and the second engaging portion 17 is perimetrically connected to the rim 5. To close the sealable carrying bag 2, the first engaging portion 16 and the second engaging portion 17 are mechanically engaged to each other. In the preferred embodiment of the present invention, the lid fastener 15 is a zipper fastener; however, other types of fasteners may alternatively be used.

Figure 4:
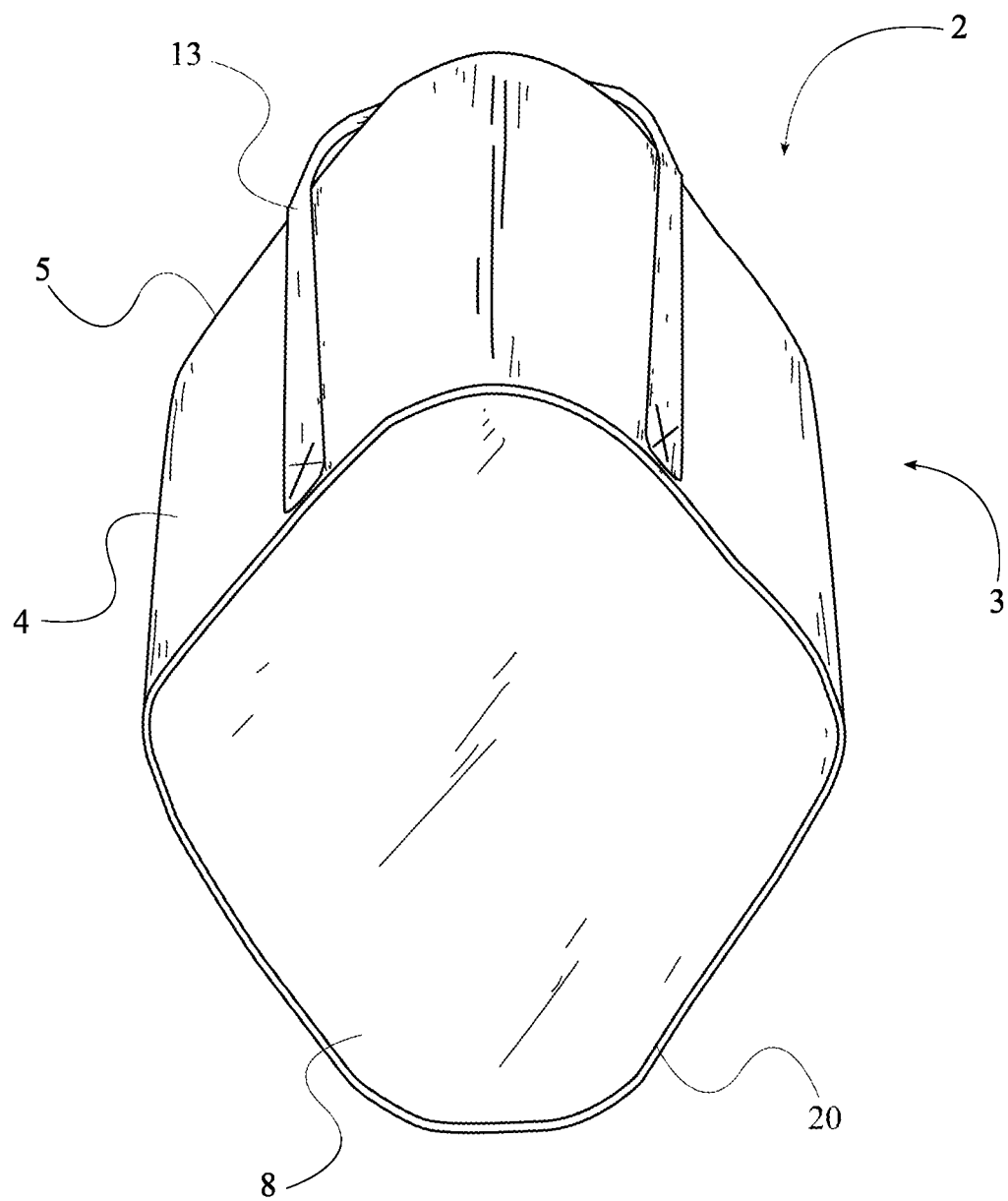
FIG. 4 is a bottom perspective view of the present invention.

In reference to FIG. 3, and FIG. 4, the present invention further comprises a lid trim 18, a lateral trim 19, a base trim 20. The lid trim 18, the lateral trim 19, and the base trim 20 are each used to reinforce the sealable carrying bag 2 and make the sealable carrying bag 2 more resistant to wear-and-tear. The lid trim 18 is perimetrically connected about the lid 12 and helps to prevent damage to the edges of the lid 12. The lateral trim 19 is perimetrically connected about the rim 5. The lateral trim 19 helps to protect the rim 5 and reinforce the rim 5 so that the infrared sauna lamp 1 may be easily put into or taken out of the sealable carrying bag 2 without the flexible receptacle 3 collapsing. The base trim 20 is perimetrically connected in between the base portion 8 and the lateral portion 4. The base trim 20 helps to ruggedize the perimeter of the base portion 8, where the most wear is generally expected. The lid trim 18, the lateral trim 19, and the base trim 20 also help to add a decorative look to the sealable carrying bag 2.

Figure 2:
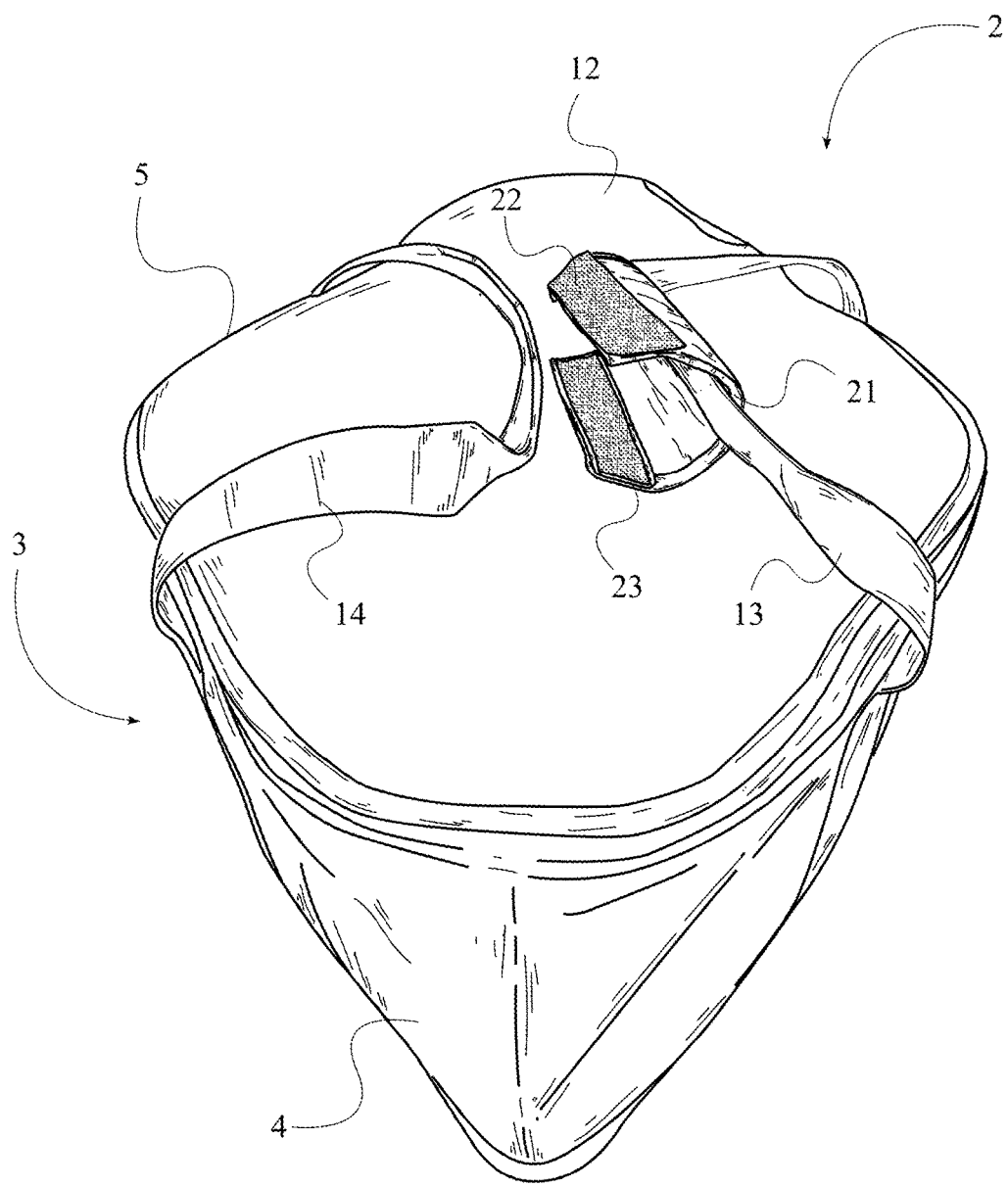
FIG. 2 is a top perspective view of the preset invention with the first handle and the second handle separated.

In reference to FIG. 1, FIG. 2, and FIG. 5, the present invention further comprises a handle grip 21, a first end fastener 22, and a second end fastener 23. The handle grip 21 is laterally connected to the first handle 13 and is used to secure the first handle 13 to the second handle 14. This is done to easily arrange both the first handle 13 and the second handle 14 for easy carrying. The handle grip 21 is centrally positioned along the first handle 13. And is designed to cover both the first handle 13 and the second handle 14. The first end fastener 22 and the second end fastener 23 are each connected adjacent to the handle grip 21. In order to secure the handle grip 21 about the first handle 13 and the second handle 14, the first end fastener 22 and the second end fastener 23 are positioned opposite to each other across and about the handle grip 21. When the handle grip 21 is wrapped around the first handle 13 and the second handle 14, the first end fastener 22 and the second end fastener 23 engage to each other, securing the handle grip 21 in place.

Figure 6:
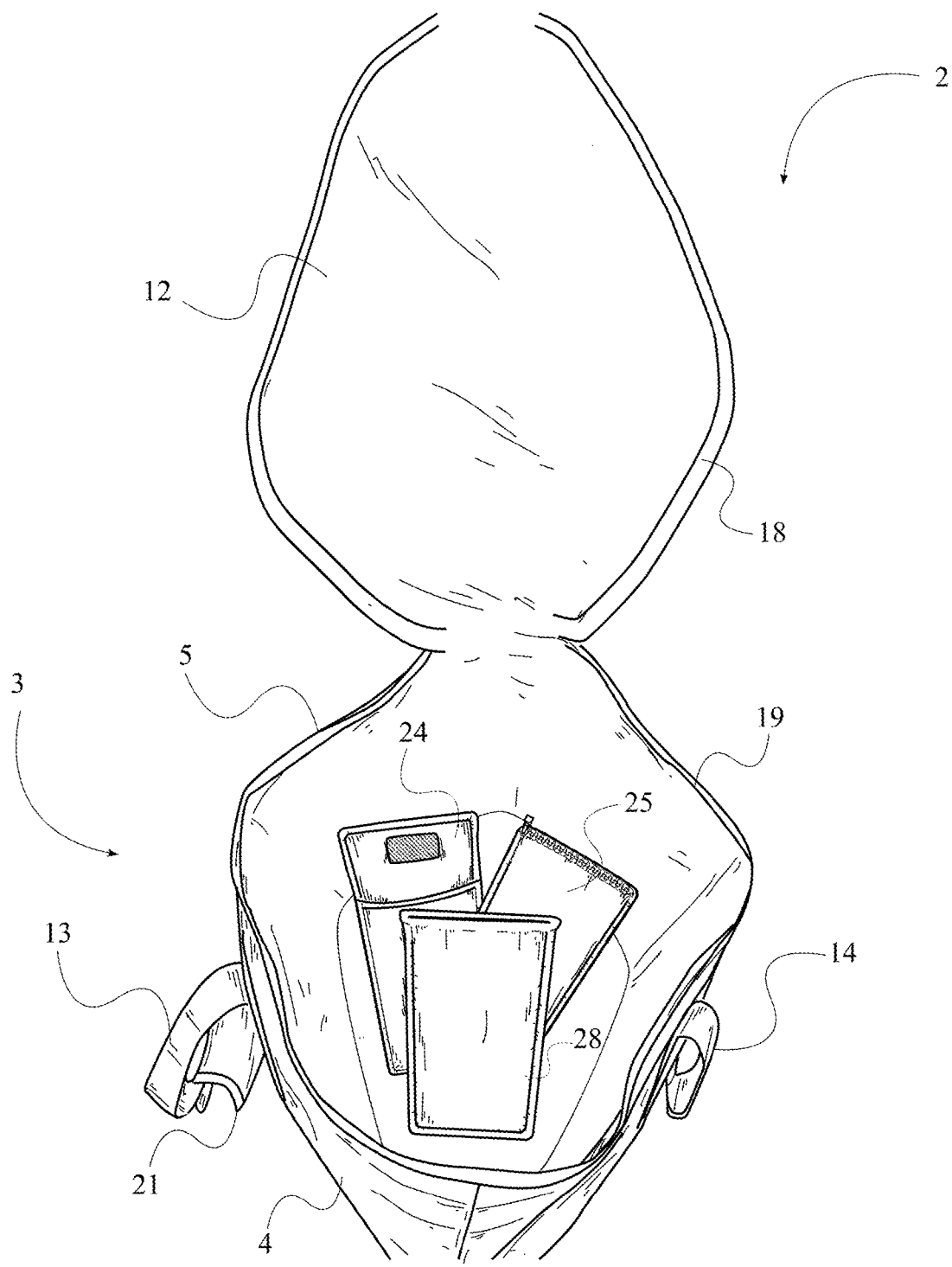
FIG. 6 is a top perspective view of the present invention with the first pouch, the second pouch, and the third pouch positioned within the sealable carrying bag.
Figure 7A:
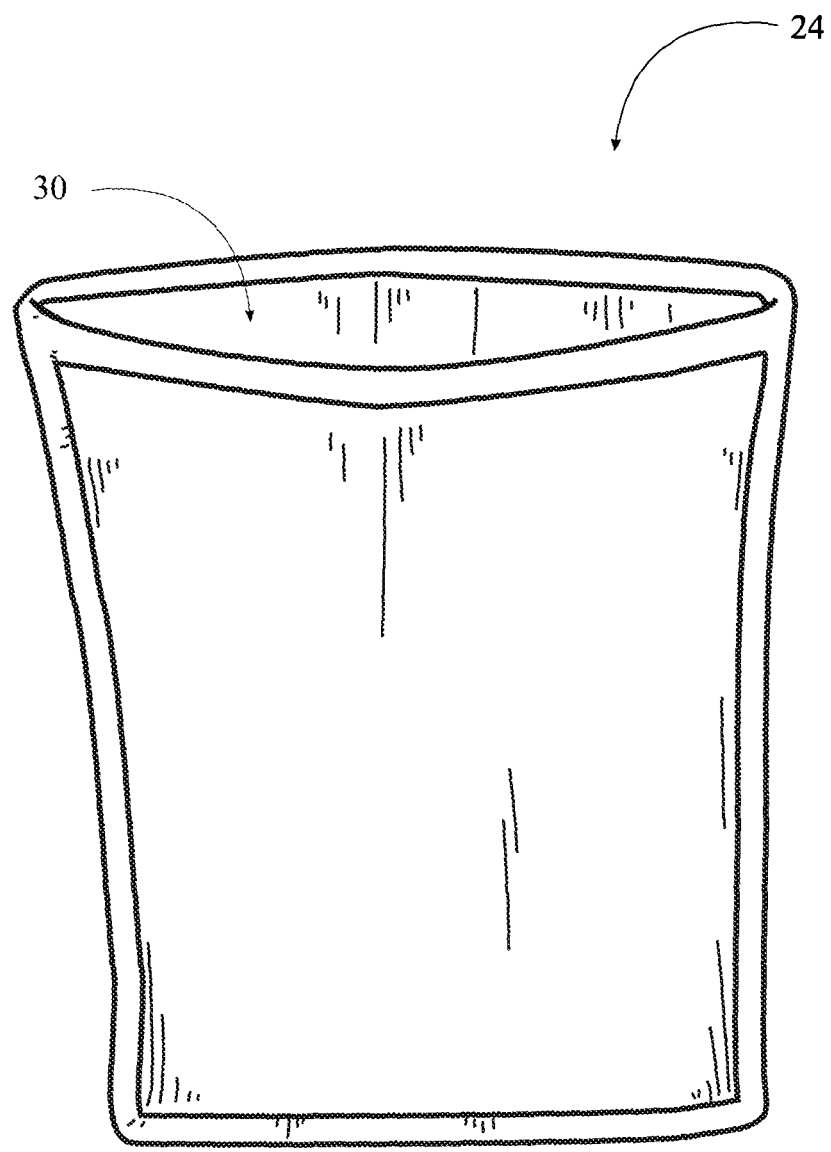
FIG. 7A is a top view of the first pouch.

In reference to FIG. 6 and FIG. 7A, the present invention further comprises a first pouch 24, a second pouch 25, and a third pouch 28. The first pouch 24, the second pouch 25, and the third pouch 28 are each used to carry various items need for operating the infrared sauna lamp 1. For example, in the preferred embodiment of the present invention, the first pouch 24 is used to hold one or more chains, or rope ratchets, used for hanging the infrared sauna lamp 1, the second pouch 25 is used to hold and manage cords attached to the infrared sauna lamp 1, and the third pouch 28 is used to hold safety glasses. Along with the infrared sauna bag, the first pouch 24, the second pouch 25, and the third pouch 28 are each positioned within the flexible receptacle 3 for easy transport.

Figure 7B:
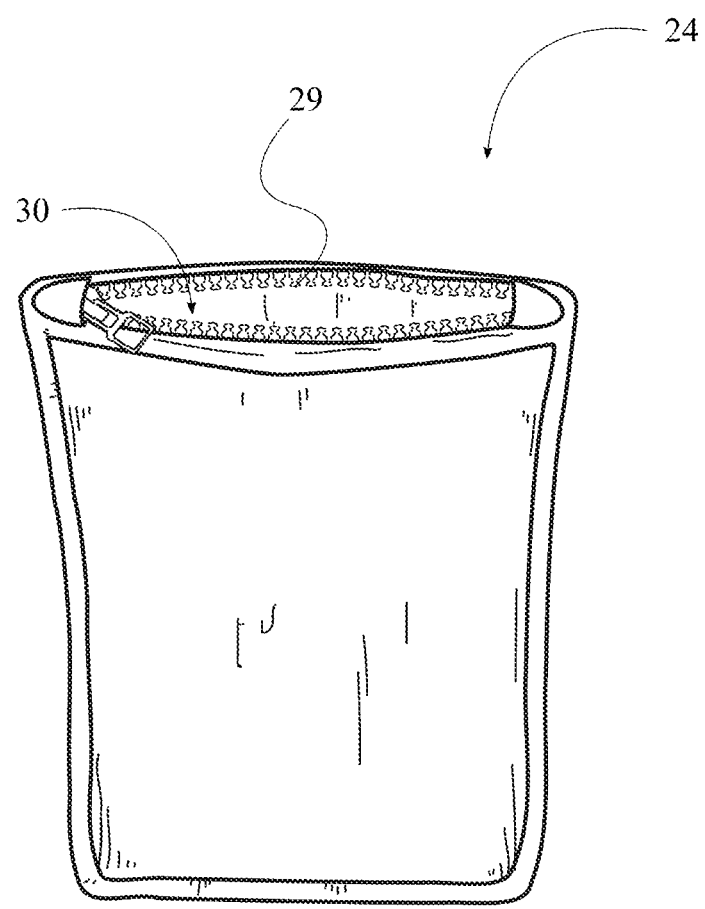
FIG. 7B is a top view of the first pouch and the first pouch fastener.

In reference to FIG. 7B, the present invention further comprises a first pouch fastener 29. The first pouch fastener 29 is used to secure items within the first pouch 24. The first pouch fastener 29 is perimetrically connected along an opening 30 of the first pouch 24. In the preferred embodiment of the present invention, the first pouch fastener 29 is a zipper fastener; however, other types of fasteners may alternatively be used.

Figure 8:
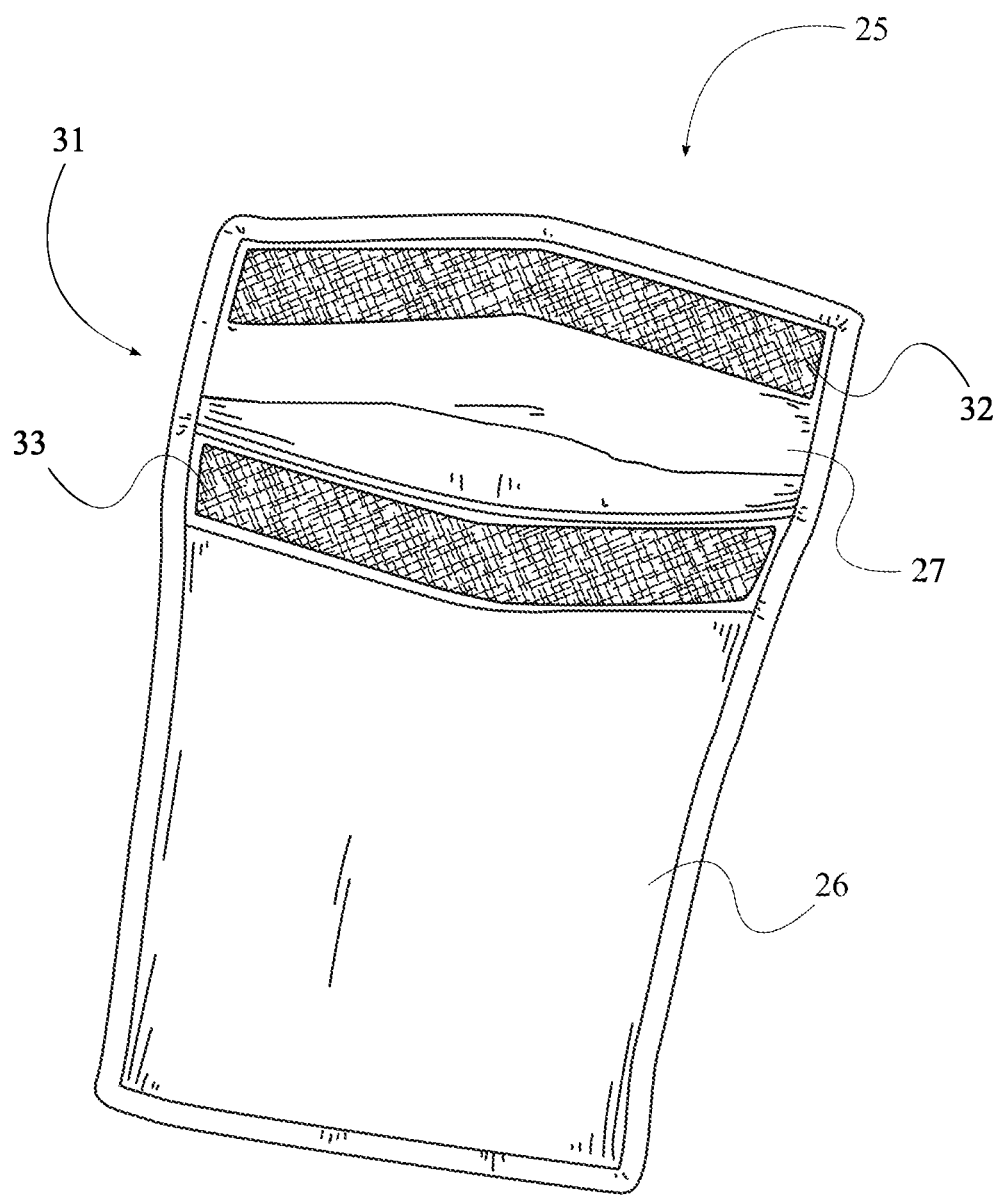
FIG. 8 is a top view of the second pouch and the second pouch fastener.

In reference to FIG. 8, the present invention further comprises a second pouch fastener 31. Similar to the first pouch fastener 29, the second pouch fastener 31 is used secure items within the second pouch 25. The second pouch 25 comprises a pocket portion 26 and a flap portion 27. Items are held within the pocket portion 26. The flap portion 27 is connected adjacent to the pocket portion 26 and may be folded over the pocket portion 26 to close the pocket portion 26. The second pouch fastener 31 comprises a first interlocking portion 32 and a second interlocking portion 33. The first interlocking portion 32 is connected adjacent to the flap portion 27, while the second interlocking portion 33 is connected adjacent to the pocket portion 26. When the flap portion 27 is folded over the pocket portion 26, the first interlocking portion 32 and the second interlocking portion 33 are engaged to each other. In the preferred embodiment of the present invention, the second pouch fastener 31 is a hook and loop fastener; however, other fastener types may alternatively be used.

Figure 9:
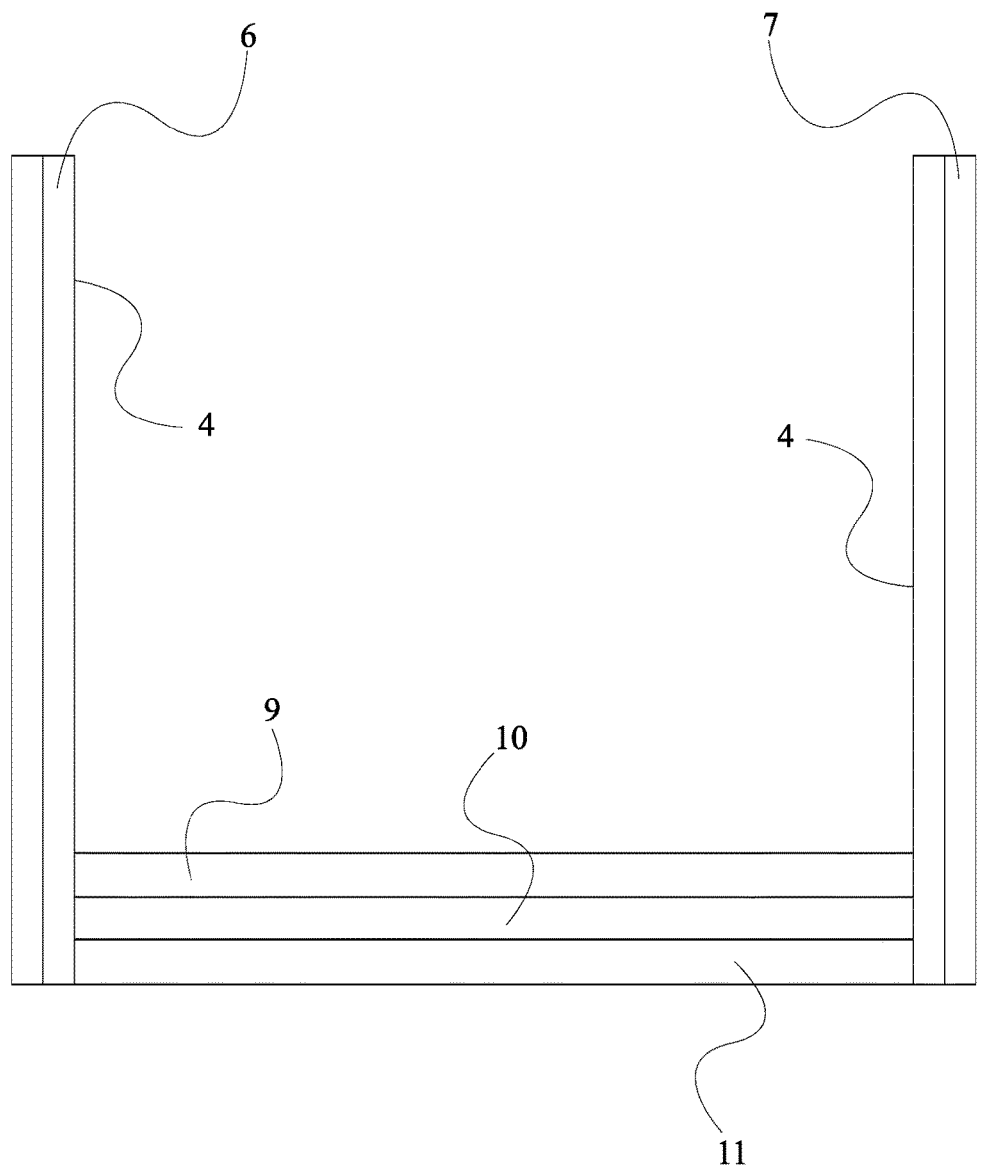
FIG. 9 is a schematic view of the flexible receptacle.

In reference to FIG. 9, the base portion 8 comprises an inner layer 9, a reinforcing layer 10, and an outer layer 11. The inner layer 9 directly contacts the infrared sauna device and is designed not to snag on any edges of the infrared sauna device. In the preferred embodiment of the present invention, the inner layer 9 is slightly cushioned to help prevent the infrared sauna bag from sustaining impact damage. The inner layer 9 is connected adjacent to the reinforcing layer 10. The reinforcing layer 10 is used to give structure to the flexible receptacle 3 and ensures that the base portion 8 remains relatively flat at all times. This helps to prevent the sealable carrying bag 2 from inadvertently tipping over. The outer layer 11 is connected adjacent to the reinforcing layer 10, opposite to the inner layer 9. The outer layer 11 is used to protect the inner layer 9, the reinforcing layer 10, and the infrared sauna device from wear. In the preferred embodiment of the present invention, the outer layer 11 is made from a durable, scratch-resistant material.

Also in reference to FIG. 9, the lateral portion 4 comprises a proximal layer 6 and a distal layer 7. The proximal layer 6 and the distal layer 7 work similar to the inner layer 9 and the outer layer 11 of the base portion 8. The proximal layer 6 helps to protect and cushion the infrared sauna device. The proximal layer 6 is connected adjacent to the distal layer 7. The distal layer 7 is concentrically aligned about the proximal layer 6 and is used to limit wear to the proximal layer 6 and the infrared sauna device.

Although the invention has been explained in relation to its preferred embodiment, it is to be understood that many other possible modifications and variations can be made without departing from the spirit and scope of the invention as hereinafter claimed.

What is claimed is:
1. A system for transporting a sauna device comprises:
an infrared sauna lamp;
a sealable carrying bag;
the sealable carrying bag comprises a flexible receptacle, a lid, a first handle, and a second handle;
the flexible receptacle comprises a lateral portion and a base portion;
the lateral portion being perimetrically connected to the base portion;
a rim of the lateral portion being perimetrically positioned about the lateral portion, opposite to the base portion;
the lid being hingedly connected to the rim;
the first handle being laterally connected to the lateral portion, in between the base portion and the rim;
the second handle being laterally connected to the lateral portion, in between the base portion and the rim;
the first handle and the second handle being positioned opposite to each other about the lateral portion;
the infrared sauna lamp being positioned within the sealable carrying bag;
a first pouch;
a second pouch;
a third pouch;
the first pouch, the second pouch, and the third pouch each being positioned within the flexible receptacle;
a pouch fastener;
the second pouch comprises a pocket portion and a flap portion;
the pouch fastener comprises a first interlocking portion and a second interlocking portion;

the flap portion being connected adjacent to the pocket portion;
the first interlocking portion being connected adjacent to the flap portion;
the second interlocking portion being connected adjacent to the pocket portion; and
the first interlocking portion and the second interlocking portion being engaged to each other.

2. The system for transporting a sauna device as claimed in claim 1 comprises:
a lid fastener;
the lid fastener comprises a first engaging portion and a second engaging portion;
the first engaging portion being perimetrically connected to the lid;
the second engaging portion being perimetrically connected to the rim; and
the first engaging portion and the second engaging portion being mechanically engaged to each other.

3. The system for transporting a sauna device as claimed in claim 1 comprises:
a lid trim; and
the lid trim being perimetrically connected about the lid.

4. The system for transporting a sauna device as claimed in claim 1 comprises:
a lateral trim; and
the lateral trim being perimetrically connected about the rim.

5. The system for transporting a sauna device as claimed in claim 1 comprises:
a base trim; and
the base trim being perimetrically connected in between the base portion and the lateral portion.

6. The system for transporting a sauna device as claimed in claim 1 comprises:
a handle grip;
a first end fastener;
a second end fastener;
the handle grip being laterally connected to the first handle;
the handle grip being centrally positioned along the first handle;
the first end fastener being connected adjacent to the handle grip;
the second end fastener being connected adjacent to the handle grip; and
the first end fastener and the second end fastener being positioned opposite to each other across and about the handle grip.

7. The system for transporting a sauna device as claimed in claim 1 comprises:
another pouch fastener; and
the another pouch fastener being perimetrically connected along an opening of the first pouch.

8. The system for transporting a sauna device as claimed in claim 1 comprises:
the base portion comprises an inner layer, a reinforcing layer, and an outer layer;
the inner layer being connected adjacent to the reinforcing layer; and
the outer layer being connected adjacent to the reinforcing layer, opposite to the inner layer.

9. The system for transporting a sauna device as claimed in claim 1 comprises:
the lateral portion comprises a proximal layer, and a distal layer;
the proximal layer being connected adjacent to the distal layer; and
the distal layer being concentrically aligned about the proximal layer.

* * * * *